(12) United States Patent
Zirwen et al.

(10) Patent No.: US 8,349,026 B2
(45) Date of Patent: Jan. 8, 2013

(54) MOUSSE-TYPE DYES II

(75) Inventors: Sabrina Zirwen, Hamburg (DE); Astrid Kleeb, Hamburg (DE); Mustafa Akram, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 13/556,465

(22) Filed: Jul. 24, 2012

(65) Prior Publication Data

US 2012/0285479 A1 Nov. 15, 2012

Related U.S. Application Data

(63) Continuation of application No. PCT/EP2010/067072, filed on Nov. 9, 2010.

(30) Foreign Application Priority Data

Jan. 29, 2010 (DE) .......................... 10 2010 001 375

(51) Int. Cl.
*A61Q 5/10* (2006.01)
(52) U.S. Cl. ............. 8/405; 8/406; 8/408; 8/410; 8/435; 8/580; 8/604
(58) Field of Classification Search ............... 8/405, 406, 8/408, 410, 435, 580, 604
See application file for complete search history.

(56) References Cited

FOREIGN PATENT DOCUMENTS

| EP | 0998908 A2 | | 5/2000 |
| JP | 10-167938 | * | 6/1998 |
| JP | 10167938 | | 6/1998 |
| WO | 2006066642 A1 | | 6/2006 |

OTHER PUBLICATIONS

English abstract of the Patent No. JP 10-167938 dated Jun. 23, 1998.*
STIC Search Report dated Sep. 19, 2012.*

* cited by examiner

*Primary Examiner* — Eisa Elhilo
(74) *Attorney, Agent, or Firm* — David LeCroy

(57) ABSTRACT

Products for dying keratin fibers comprising, in a cosmetically acceptable carrier, at least one oxidation dye precursor and at least one alkanolamine, the product containing at least one zwitterionic surfactant according to formula (I)—

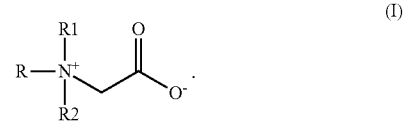

14 Claims, No Drawings

MOUSSE-TYPE DYES II

CROSS REFERENCE TO RELATED APPLICATIONS

The present application is a continuation of International Application No. PCT/EP2010/067072 filed 9 Nov. 2010, which claims priority to German Patent Application No. 10 2010 001 375.7, filed Jan. 29, 2010, both of which are incorporated herein by reference.

BACKGROUND OF THE INVENTION

The invention relates to dyeing agents having a special zwitterionic surfactant and which are suitable for being applied in the form of stable foam by special application devices, a dyeing process involving the use of the agent and the application device, as well as a corresponding kit for dyeing keratin-containing fibers.

Generally, either substantive dyes or oxidation dyes resulting from oxidative coupling of one or more developer components with each other or with one or more coupler components are used for dyeing fibers containing keratin. Coupler components and developer components are also called oxidation dye precursors. The developer components are normally primary aromatic amines with an additional free or substituted hydroxyl or amino group in the para or ortho position, diaminopyridine derivatives, heterocyclic hydrazones, 4-aminopyrazolone derivatives as well as 2,4,5,6-tetraminopyrimidine and derivatives thereof. m-Phenylenediamine derivatives, naphthols, resorcinol and resorcinol derivatives, pyrazolones, m-amino phenols and substituted pyridine derivatives are generally used as the coupling components.

In order to stabilize the dye precursors during storage and for accelerating the reaction during the oxidative application, oxidation dyes mostly exhibit an alkaline pH value that is adjusted with alkalizing agents, such as alkanolamines, ammonia or inorganic bases. Although ammonia in particular enables good dyeing results, it also manifests disadvantages for the user due to its odor and irritation potential for skin and mucous membranes. Consequently, increased efforts have been made to develop efficient oxidative dyes that dispense without the use of ammonia.

Oxidative dyes usually consist of a mixture of two components, with the mixture being sufficiently viscous to allow it to be comfortably applied onto hair without any dripping or running. There have also been frequent attempts to develop other presentation forms. Thus, it has been proposed to deposit lower viscosity dyes onto the hair with special applicator systems or to apply dyes as foam. In particular, the use of aerosol foams is widespread for foam application. Recently however, there has been a requirement to eliminate the use of propellant gases.

Another problem associated with foam application is stabilization of the foam. The consistency of foams is considered to be ideal when the dispensed product affords solid, stable foam that leaves a supple feel and breaks down only slowly on the hair. It is frequently observed, however, that the applied foams possess little stability and rapidly collapse, leaving behind a low viscosity solution that drips. Still, it is also important that the foam wets the hair well so that a good color application can be realized. Foam stability is negatively influenced in particular by the presence of larger amounts of salts and dye (precursor)(s). Hair treatment agents in the form of foams are already known from JP 10-167938 A. Betaine surfactants of the alkyl dimethyl betaine type and the (fatty acid amidoalkyl) dialkyl betaine type, such as cocoamidopropyl betaine, are disclosed as particularly suitable surfactants for a stable foam formation of acidic, hydrogen peroxide-containing hair treatment agents. Cocoamidopropyl betaine is also described in WO 2006/066642(A1) as a suitable surfactant with high surfactant content in tinting foams based on substantive dyes.

However, it has been shown in extensive tests that the strongly alkaline oxidation dye preparations pose particular challenges to the foam-forming surfactant. In particular, foaming oxidation dye preparations with high amounts of fatty acid amidoalkyl betaines as the foam-forming surfactant tend to develop amine-like odors, particularly in the presence of alkanolamines as the alkalizing agent, which are perceived by the user as disturbing and unpleasant.

SUMMARY OF THE INVENTION

Accordingly, the present invention optimizes oxidation dyes for foam application without use of propellant gases, so that the above cited disadvantages are overcome. In particular, stable dyeing foams without unpleasant odors are provide which, to the extent possible, are free of ammonia.

It was surprisingly found that oxidation dyes having a special, zwitterionic surfactant and an alkanolamine as the alkalizing agent provide extremely stable foams that enable a simple and intensive coloration of the fibers. Stability is conserved even with higher salt concentrations. Moreover, agents according to the invention enable more intensive coloration results and significantly longer-lasting coloration results than did previously known foam preparations. Finally, the agents are low in odor.

DETAILED DESCRIPTION OF THE INVENTION

Accordingly, a first subject matter of the present invention is agents for dyeing keratinic fibers comprising in a cosmetically acceptable carrier at least one oxidation dye precursor as well as at least one alkanolamine, the agent further comprising at least one zwitterionic surfactant according to Formula (I)—

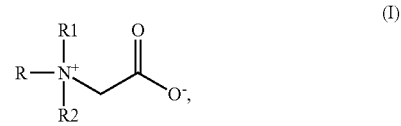

wherein
R is a saturated or unsaturated $C_{10}$-$C_{20}$ alkyl chain, and
R1 and R2 are each independently a $C_1$-$C_4$ alkyl group or a $C_2$-$C_4$ hydroxyalkyl group.

Keratin-containing fibers refer to wool, furs, feathers and particularly human hair. However, the inventive dyes can, in principle, also be used for dyeing other natural fibers (e.g., cotton, jute, sisal, linen or silk), modified natural fibers, such as cellulose regenerate, nitrocellulose, alkyl cellulose or hydroxyalkyl cellulose or acetyl cellulose.

Agents according to the invention comprise the active substances in a cosmetically acceptable carrier. This cosmetic carrier is preferably aqueous, alcoholic or aqueous-alcoholic. According to the invention, an aqueous carrier comprises at least 40 wt %, especially at least 50 wt % water. For the purposes of the present invention, aqueous-alcoholic carriers are water-containing compositions comprising 3 to 70 wt % of a $C_1$-$C_4$ alcohol, particularly ethanol or isopropanol.

Agents according to the invention can also comprise further organic solvents such as 4-methoxybutanol, ethyl diglycol, 1,2-propylene glycol, n-propanol, n-butanol, n-butylene glycol, glycerin, diethylene glycol monoethyl ether, and diethylene glycol mono-n-butyl ether, in so far as foam formation and foam stability are not excessively negatively influenced. Preference here is given to all water-soluble organic solvents. Preferred inventive agents additionally comprise a non-aqueous solvent, wherein particularly preferred inventive agents comprise the solvent in a concentration of 0.1 to 30 wt %, preferably 1 to 20 wt %, quite particularly preferably 2 to 10 wt %, based on weight of the agent.

As a first component the agents comprise at least one oxidation dye precursor. The agent preferably comprises one or more developer components, as well as optionally one or more coupler components.

Under the influence of oxidizing agents or from atmospheric oxygen, the developer components form the actual colorants among each other or by coupling with one or more coupler components. The developer components that are used are usually primary aromatic amines with an additional free or substituted hydroxyl or amino group in the para or ortho position, diaminopyridine derivatives, heterocyclic hydrazones, 4-aminopyrazolone derivatives as well as 2,4,5,6-tetraminopyrimidine and derivatives thereof. According to the invention, it may be preferred to use a p-phenylenediamine derivative or one of its physiologically acceptable salts as the developer component. Particular preference is given to p-phenylenediamine derivatives of formula (E1)—

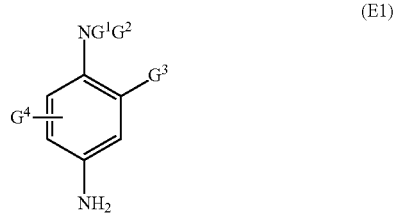

(E1)

wherein
G$^1$ is a hydrogen atom, a C$_1$-C$_4$ alkyl group, a C$_1$-C$_4$ monohydroxyalkyl group, a C$_2$-C$_4$ polyhydroxyalkyl group, a (C$_1$-C$_4$) alkoxy (C$_1$-C$_4$) alkyl group, a 4'-aminophenyl group or a C$_1$-C$_4$ alkyl group that is substituted by a nitrogen-containing group, a phenyl group or a 4'-aminophenyl group;
G$^2$ is a hydrogen atom, a C$_1$-C$_4$ alkyl group, a C$_1$-C$_4$ monohydroxyalkyl group, a C$_2$-C$_4$ polyhydroxyalkyl group, a C$_1$-C$_4$ alkoxy (C$_1$-C$_4$) alkyl group or a C$_1$-C$_4$ alkyl group that is substituted by a nitrogen-containing group;
G$^3$ is a hydrogen atom, a halogen atom, such as a chlorine, bromine, iodine or fluorine atom, a C$_1$-C$_4$ alkyl group, a C$_1$-C$_4$ monohydroxyalkyl group, a C$_2$-C$_4$ polyhydroxyalkyl group, a C$_1$-C$_4$ hydroxyalkoxy group, a C$_1$-C$_4$ alkoxy-(C$_1$-C$_4$) alkyl group, a C$_1$-C$_4$ acetylaminoalkoxy group, a mesylamino-(C$_1$-C$_4$) alkoxy group or a C$_1$-C$_4$ carbamoylaminoalkoxy group; and
G$^4$ is a hydrogen atom, a halogen atom or a C$_1$-C$_4$ alkyl group or a C$_1$-C$_4$ alkoxy-(C$_1$-C$_4$) alkyl group, or
if G$^3$ and G$^4$ are in the ortho position relative to one another, they can together form a bridging a,ω-alkylenedioxo group, such as an ethylenedioxy group.

Preferred p-phenylenediamines according to Formula (E1) are chosen from one or more of p-phenylenediamine, p-toluoylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)-aniline, N,N-bis-(2-hydroxyethyl)-p-phenylenediamine, 4-N,N-bis-(2-hydroxyethyl)-amino-2-methylaniline, 4-N,N-bis-(2-hydroxyethyl)-amino-2-chloroaniline, 2-(2-hydroxyethyl)-p-phenylenediamine, 2-(1,2-dihydroxyethyl)-p-phenylenediamine, 2-fluoro-p-phenylenediamine, 2-isopropyl-p-phenylenediamine, N-(2-hydroxypropyl)-p-phenylenediamine, 2-hydroxymethyl-p-phenylenediamine, N,N-dimethyl-3-methyl-p-phenylenediamine, N-ethyl-N-2-hydroxyethyl-p-phenylenediamine, N-(2,3-dihydroxypropyl)-p-phenylenediamine, N-(4'-aminophenyl)-p-phenylenediamine, N-phenyl-p-phenylenediamine, 2-(2-hydroxyethyloxy)-p-phenylenediamine, 2-methoxymethyl-p-phenylenediamine, 2-(2-acetylaminoethyloxy)-p-phenylenediamine, N-(2-methoxyethyl)-p-phenylenediamine, N-(4-amino-3-methylphenyl)-N-[3-(1H-imidazol-1-yl)propyl]amine, 5,8-diaminobenzo-1,4-dioxane as well as their physiologically acceptable salts. Inventively particularly preferred p-phenylenediamine derivatives are selected from at least one compound of the group p-phenylenediamine, p-toluoylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, N-(4-amino3-methylphenyl)-N-[3-(1H-imidazol-1-yl)propyl]amine, 2-methoxymethyl-p-phenylenediamine as well as the physiologically acceptable salts of these compounds.

According to the invention, it may also be preferred to use as the developer component compounds which have at least two aromatic nuclei that are substituted by amino and/or hydroxyl groups.

Among the binuclear developer components that can be used in colorant compositions according to the invention, mention may be made in particular of those compounds which conform to the following formula (E2), together with their physiologically compatible salts,

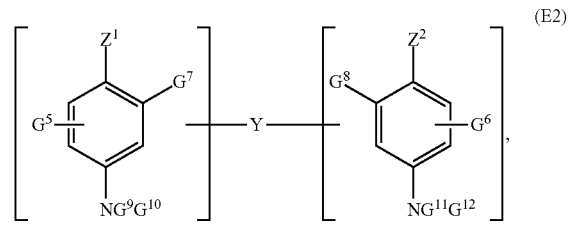

(E2)

wherein
Z$^1$ and Z$^2$ are independently a hydroxyl or NH$_2$ group, which is optionally substituted by a C$_1$-C$_4$ alkyl group, a C$_1$-C$_4$ hydroxyalkyl group and/or a bridge Y, or which is optionally part of a bridging ring system,
the bridge Y is an alkylene group containing 1 to 14 carbon atoms, such as a linear or branched alkylene chain or an alkylene ring which can be interrupted or terminated by one or more nitrogen-containing groups and/or one or more heteroatoms (e.g., oxygen, sulfur or nitrogen atoms) and may possibly be substituted by one or more hydroxyl or C$_1$-C$_8$ alkoxy groups, or is a direct bond,
G$^5$ and G$^6$ are independently a hydrogen or halogen atom, a C$_1$-C$_4$ alkyl group, a C$_1$-C$_4$ monohydroxyalkyl group, a C$_2$-C$_4$ polyhydroxyalkyl group, a C$_1$-C$_4$ aminoalkyl group or a direct bond to the bridge Y, G⁷, G⁸, G₉, G¹⁰, G¹¹ and G¹² are independently a hydrogen atom, a direct bond to the bridge Y, or a $C_1$-$C_4$ alkyl group, with the proviso that the compounds of Formula (E2) comprise only one bridge Y per molecule.

Preferred binuclear developer components of Formula (E2) are especially chosen from at least one of the following compounds: N,N'-bis-(2-hydroxyethyl)-N,N'-bis-(4-aminophenyl)-1,3-diamino-propan-2-ol, N,N-bis-(2-hydroxyethyl)-N,N'-bis-(4-aminophenyl)ethylenediamine, N,N'-bis-(4-aminophenyl)tetramethylenediamine, N,N'-bis-(2-hydroxyethyl)-N,N'-bis-(4-aminophenyl) tetramethylenediamine, N,N'-bis-(4-(methylamino)phenyl) tetramethylenediamine, N,N'-diethyl-N,N'-bis-(4-amino-3-methylphenyl)ethylenediamine, bis-(2-hydroxy-5-aminophenyl)methane, N,N'-bis(4-aminophenyl)-1,4-diazacycloheptane, N,N'-bis-(2-hydroxy-5-aminobenzyl) piperazine, N-(4-aminophenyl)-p-phenylenediamine and 1,10-bis-(2',5'-diaminophenyl)-1,4,7,10-tetraoxadecane as well as their physiologically acceptable salts. Quite particularly preferred binuclear developer components of Formula (E2) are selected from among N,N'-bis-(2-hydroxyethyl)-N, N'-bis-(4-aminophenyl)-1,3-diamino-2-propanol, bis-(2-hydroxy-5-aminophenyl)methane, 1,3-bis-(2,5-diaminophenoxy)-2-propanol, N,N'-bis(4-aminophenyl)-1,4-diazacycloheptane, 1,10-bis-(2,5-diaminophenyl)-1,4,7,10-tetraoxadecane or one of their physiologically acceptable salts.

Moreover, according to the invention, it may be preferred to use a p-aminophenol derivative or one of its physiologically acceptable salts as the developer component. p-Amino phenol derivatives of Formula (E3) are particularly preferred—

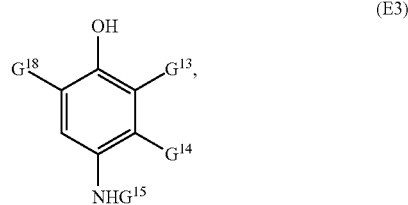

(E3)

wherein
G¹³ is a hydrogen atom, a halogen atom, a $C_1$-$C_4$ alkyl group, a $C_1$-$C_4$ monohydroxyalkyl group, a $C_2$-$C_4$ polyhydroxyalkyl group, a $C_1$-$C_4$ alkoxy-($C_1$-$C_4$) alkyl group, a $C_1$-$C_4$ aminoalkyl group, a hydroxy ($C_1$-$C_4$) alkylamino group, a $C_1$-$C_4$ hydroxyalkoxy group, a $C_1$-$C_4$ hydroxyalkyl ($C_1$-$C_4$) aminoalkyl group, or a di-[($C_1$-$C_4$) alkyl]amino $C_1$-$C_4$ alkyl group,
G¹⁴ is a hydrogen or halogen atom, a $C_1$-$C_4$ alkyl group, a $C_1$-$C_4$ monohydroxyalkyl group, a $C_2$-$C_4$ polyhydroxyalkyl group, a $C_1$-$C_4$ alkoxy-($C_1$-$C_4$) alkyl group, a $C_1$-$C_4$ aminoalkyl group or a $C_1$-$C_4$ cyanoalkyl group,
G¹⁵ is hydrogen, a $C_1$-$C_4$ alkyl group, a $C_1$-$C_4$ monohydroxyalkyl group, a $C_2$-$C_4$ polyhydroxyalkyl group, a phenyl group or a benzyl group, and
G¹⁶ is hydrogen or a halogen atom.

Preferred p-aminophenols of Formula (E3) are especially p-aminophenol, N-methyl-p-aminophenol, 4-amino-3-methyl-phenol, 4-amino-3-fluorophenol, 2-hydroxymethylamino-4-aminophenol, 4-amino-3-hydroxymethylphenol, 4-amino-2-(2-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-(2-hydroxyethylaminomethyl)phenol, 4-amino-2-(1,2-dihydroxyethyl)phenol, 4-amino-2-fluorophenol, 4-amino-2-chlorophenol, 4-amino-2,6-dichlorophenol, 4-amino-2-(diethylaminomethyl)phenol as well as their physiologically acceptable salts. p-Aminophenol, 4-amino-3-methylphenol, 4-amino-2-aminomethylphenol, 4-amino-2-(1,2-dihydroxyethyl)phenol and 4-amino-2-(diethylaminomethyl)phenol are particularly preferred compounds of the Formula (E3). Furthermore, the developer component can be chosen from o-aminophenol and its derivatives, such as 2-amino-4-methylphenol, 2-amino-5-methylphenol or 2-amino-4-chlorophenol. In addition, the developer component can be chosen from heterocyclic developer components, for example, from pyrimidine derivatives, pyrazole derivatives, pyrazole-pyrimidine derivatives and their physiologically acceptable salts. Particularly preferred pyrimidine derivatives include the compounds 2,4,5,6-tetraminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine and 2,5,6-triaminopyrimidine. Particularly preferred pyrazole derivatives include compounds chosen from 4,5-diamino-1-methylpyrazole, 4,5-diamino-1-(β-hydroxyethyl)-pyrazole, 3,4-diaminopyrazole, 4,5-diamino-1-(4-chlorobenzyl)-pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(6-hydroxyethyl)-3-methylpyrazole, 4,5-diamino-1-ethyl-3-methylpyrazole, 4,5-diamino-1-ethyl-3-(4-methoxyphenyl)-pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2-aminoethyl)amino-1,3-dimethylpyrazole as well as their physiologically acceptable salts. Preferred pyrazolopyrimidines are pyrazolo[1,5-a]-pyrimidines. Particularly preferred pyrazolo[1,5-a]pyrimidines are again pyrazolo[1,5-a]pyrimidine-3,7-diamine, 2,5-dimethyl-pyrazolo[1,5-a]pyrimidine-3,7-diamine, pyrazolo[1,5-a]pyrimidine-3,5-diamine, 2,7-dimethyl-pyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)-(2-hydroxyethyl)-amino]-ethanol, 2-[(7-aminopyrazolo[1,5-a]pyrimidin-3-yl)-(2-hydroxy-ethyl)-amino]-ethanol, 5,6-dimethylpyrazolo[1,5-a]pyrimidine-3,7-diamine, 2,6-dimethylpyrazolo[1,5-a]pyrimidine-3,7-diamine, 3-amino-7-dimethylamino-2,5-dimethylpyrazolo[1,5-a]pyrimidine as well as their physiologically acceptable salts and their tautomeric forms, if a tautomeric equilibrium exists.

Quite particularly preferred developer components are chosen from at least one compound from p-phenylenediamine, p-toluoylenediamine, 2-(2-hydroxy-ethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diamino-2-propanol, bis-(2-hydroxy-5-aminophenyl)methane, 1,3-bis-(2,5-diaminophenoxy)-2-propanol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxy-ethyl)phenol and 4-amino-2-(diethylaminomethyl)phenol, 4,5-diamino-1-(2-hydroxyethyl)pyrazole, 2,4,5,6-tetraminopyrimidine, 4-hydroxy-2,5,6-triaminopyrimidine, 2-hydroxy-4,5,6-triaminopyrimidine, as well as the physiologically acceptable salts of these compounds.

Developer components are preferably used in an amount of 0.005 to 20 wt %, preferably 0.1 to 5 wt %, based on the ready-to-use oxidation dye.

Coupler components alone, in the context of the oxidative dyeing, do not form any significant coloration; rather they need the presence of developer components. Therefore it is inventively preferred that when using at least one coupler component, at least one developer component is also used.

According to the invention, coupler components allow at least one substitution of a chemical group of the coupler by the oxidized form of the developer component. A covalent bond is formed between coupler component and developer component. Couplers are preferably cyclic compounds having at least two groups on the ring, chosen from (i) optionally substituted amino groups and/or (ii) hydroxyl groups. These groups are conjugated through a double bond system.

Coupler components according to the invention are preferably chosen from m-aminophenol and/or its derivatives, m-diaminobenzene and/or its derivatives, o-diaminobenzene and/or its derivatives, o-aminophenol and/or its derivatives, naphthalene derivatives with at least one hydroxyl group, di- or trihydroxybenzene and/or its derivatives, pyridine derivatives, pyrimidine derivatives, monohydroxyindole derivatives and/or monoaminoindole derivatives, monohydroxyindoline derivatives and/or monoaminoindoline derivatives, pyrazolone derivatives, such as 1-phenyl-3-methylpyrazol-5-one, morpholine derivatives such as 6-hydroxybenzomorpholine or 6-aminobenzomorpholine, quinoxaline derivatives such as 6-methyl-1,2,3,4-tetra-hydroquinoxaline, as well as mixtures of two or more compounds from one or more of these classes.

Preferred m-aminophenol coupler components are chosen from at least one compound of m-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)-amino-2-methylphenol, 3-diethylaminophenol, N-cyclopentyl-3-aminophenol, 1,3-dihydroxy-5-(methylamino)benzene, 3-ethylamino-4-methylphenol, 2,4-dichloro-3-aminophenol and their physiologically acceptable salts. Preferred m-diaminobenzene coupler components are chosen from at least one compound of 2-(2,4-diaminophenoxy)ethanol, 1,3-bis(2,4-diaminophenoxy)propane, 1-methoxy-2-amino-4-(2'-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxy-ethoxy)-5-methylphenylamine, 1-amino-3-bis-(Z-hydroxyethyl)aminobenzene and their physiologically acceptable salts. Preferred o-diaminobenzene coupler components are chosen from at least one compound from 3,4-diaminobenzoic acid and 2,3-diamino-1-methylbenzene and their physiologically acceptable salts. Preferred di- or trihydroxybenzenes and their derivatives are chosen from at least one compound of resorcinol, resorcinol monomethyl ether, 2-methylresorcinol, 5-methylresorcinol, 2,5-dimethylresorcinol, 2-chlororesorcinol, 4-chlororesorcinol, pyrogallol and 1,2,4-trihydroxybenzene. Preferred pyridine derivatives are chosen from at least one compound of 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 3,4-diaminopyridine, 2-(2-methoxyethyl)amino-3-amino-6-methoxypyridine, 2-(4'-methoxyphenyl)amino-3-aminopyridine, and their physiologically acceptable salts. Preferred naphthalene derivatives with at least one hydroxyl group are chosen from at least one compound of 1-naphthol, 2-methyl-1-naphthol, 2-hydroxymethyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-dihydroxynaphthalene. Preferred indole derivatives are chosen from at least one compound of 4-hydroxyindole, 6-hydroxyindole and 7-hydroxyindole and their physiologically acceptable salts. Preferred indoline derivatives are chosen from at least one compound of 4-hydroxyindoline, 6-hydroxyindoline and 7-hydroxyindoline and their physiologically acceptable salts. Preferred pyrimidine derivatives are chosen from at least one compound of 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine and their physiologically acceptable salts.

Inventively particularly preferred coupler components are chosen from m-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2-hydroxyethyl)amino-2-methylphenol, 3-(diethylamino)phenol, N-cyclopentyl-3-aminophenol, 1,3-dihydroxy-5-(methylamino)benzene, 3-ethylamino-4-methylphenol, 2,4-dichloro-3-aminophenol, 2-(2,4-diaminophenoxy)ethanol, 1,3-bis-(2,4-diaminophenoxy)propane, 1-methoxy-2-amino-4-(2-hydroxyethylamino)benzene, 1,3-bis-(2,4-diaminophenyl)propane, 2,6-bis-(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, resorcinol monomethyl ether, 2-methylresorcinol, 5-methylresorcinol, 2,5-dimethylresorcinol, 2-chlororesorcinol, 4-chlororesorcinol, pyrogallol, 1,2,4-trihydroxybenzene, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 2,6-dihydroxy-3,4-dimethylpyridine, 3,4-diaminopyridine, 2-(2-methoxyethyl)amino-3-amino-6-methoxypyridine, 2-(4'-methoxyphenyl)amino-3-aminopyridine, 1-naphthol, 2-methyl-1-naphthol, 2-hydroxymethyl-1-naphthol, 2-hydroxyethyl-1-naphthol, 1,3-dihydroxynaphthalene, 1,5-dihydroxynaphthalene, 1,6- dihydroxynaphthalene, 1,7-dihydroxynaphthalene, 1,8-dihydroxynaphthalene, 2,7-dihydroxynaphthalene, 2,3-dihydroxynaphthalene, 4-hydroxyindole, 6-hydroxyindole, 7-hydroxyindole, 4-hydroxyindoline, 6-hydroxyindoline, 7-hydroxyindoline, 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine or mixtures of these compounds or their physiologically acceptable salts.

Coupler components are preferably used in an amount of 0.005 to 20 wt %, more preferably 0.1 to 5 wt %, based on the ready-to-use oxidation dye.

Here, developer components and coupler components are generally used in approximately molar amounts relative to one another. Although molar use has proven to be expedient, a certain excess of individual oxidation dye precursors is not disadvantageous, meaning that developer components and coupler components may be present in a molar ratio of from 1 to 0.5 to 1 to 3, particularly 1 to 1 to 1 to 2.

In order to provide further nuances of the resulting color tints it can be inventively preferred to additionally incorporate at least one substantive dye in the agent. These are dye molecules that are directly absorbed onto the substrate and do not require any oxidative process to develop the color. These dyes include, for example, Henna that was already known in antiquity for dyeing skin and hair. Nowadays substantive dyes are usually nitrophenylenediamines, nitroaminophenols, azo dyes, anthraquinones or indophenols.

The substantive dyes are each preferably used in amounts of 0.001 to 20 wt %, based on total end-use preparation. The total amount of substantive dyes is preferably a maximum of 20 wt %. Substantive dyes can be divided into anionic, cationic and non-ionic substantive dyes.

Preferred anionic substantive dyestuffs are known compounds with the international designations or trade names Acid Yellow 1, Acid Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1 and Acid Black 52 as well as Tetrabromophenol blue and Bromophenol blue.

Preferred cationic substantive dyes include—
  (a) cationic triphenylmethane dyes such as Basic Blue 7, Basic Blue 26, Basic Violet 2 and Basic Violet 14;
  (b) aromatic systems which are substituted by a quaternary nitrogen group, such as Basic Yellow 57, Basic Red 76, Basic Blue 99, Basic Brown 16 and Basic Brown 17; and
  (c) substantive dyes comprising a heterocycle having at least one quaternary nitrogen atom, as specified, for example, in EP-A2-998 908 in claims 6 to 11. The compounds, which are also known under the names Basic Yellow 87, Basic Orange 31 and Basic Red 51, are quite particularly preferred cationic substantive dyes.

Cationic substantive dyes commercialized under the trade name Arianor® are likewise quite particularly preferred cationic substantive dyes according to the invention.

Preferred non-ionic substantive dyes include known compounds with the international designations or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl) amino-4-nitrobenzene, 2-[(4-amino-2-nitrophenyl)amino]-benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-4-nitrophenol.

It is not required that each of the substantive dyestuffs be pure compounds. In fact, due to manufacturing processes for the individual dyes, minor quantities of additional components may be present, as long as they have no detrimental influence on the coloration result or must be excluded on other grounds (e.g., toxicological).

Additionally, naturally occurring dyestuffs may also be added as found, for example, in henna red, henna neutral, henna black, camomile leaves, sandalwood, black tea, alder buckthorn bark, sage, logwood, madder root, cachou and alkanet root.

Furthermore, in order to provide additional nuances, it has proven to be advantageous if agents according to the invention additionally comprise one or more dye precursors of nature-analogous dyes. The dyestuff precursors of nature-analogous dyes that are used are preferably indoles and indolines which have at least two groups chosen from hydroxyl and/or amino groups, preferably as a substituent on the six-membered ring. These groups can carry further substituents, for example, in the form of an etherified or esterified hydroxyl group or an alkylated amino group. In another embodiment, the dyes comprise at least one indole and/or indoline derivative. Compositions according to the invention having precursors of nature-analogous dyes are preferably used as the atmospherically oxidative dye. In this embodiment, an additional oxidizing agent is consequently not added to the cited compositions.

Derivatives of 5,6-dihydroxyindoline are particularly well suited as precursors of nature-analogous hair dyes. Particularly preferred derivatives of indoline are 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline as well as 5,6-dihydroxyindoline-2-carboxylic acid. In addition, derivatives of 5,6-hydroxyindole are exceptionally suitable as precursors of nature-analogous hair dyes. Preferred derivatives of indole are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid.

As a second component, agents according to the invention have at least one alkanolamine as the alkalizing agent.

Inventively useable alkanolamines are preferably chosen from alkanolamines from primary, secondary or tertiary amines containing a $C_2$-$C_8$ alkyl parent substance that carries at least one hydroxyl group. Particularly preferred alkanolamines are chosen from 2-aminoethan-1-ol (monoethanolamine), 3-aminopropan-1-ol, 4-aminobutan-1-ol, 5-aminopentan-1-ol, 1-aminopropan-2-ol (monoisopropanolamine), 1-aminobutan-2-ol, 1-aminopentan-2-ol, 1-aminopentan-3-ol, 1-aminopentan-4-ol, 2-amino-2-methyl-propanol, 2-amino-2-methylbutanol, 3-amino-2-methylpropan-1-ol, 1-amino-2-methylpropan-2-ol, 3-aminopropane-1,2-diol, 2-amino-2-methylpropane-1,3-diol, 2-amino-2-ethyl-1,3-propane diol, N,N-dimethylethanolamine, methylglucamine, triethanolamine, diethanolamine and triisopropanolamine. Inventively quite particularly preferred alkanolamines are chosen from 2-aminoethan-1-ol, 2-amino-2-methylpropan-1-ol and 2-amino-2-methyl-propane-1,3-diol. Particularly preferred agents comprise at least monoethanolamine as the alkanolamine.

Alkanolamines are preferably present in an amount of 0.05 to 20 wt %, particularly 0.5 to 15 wt %, based on total weight of the ready-to-use agent.

As a third component, dyes according to the invention comprise at least one zwitterionic surfactant of Formula (I)—

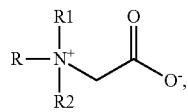

wherein
R is a saturated or unsaturated $C_{10}$-$C_{20}$ alkyl chain, and
R1 and R2 are each independently a $C_1$-$C_4$ alkyl group or a $C_2$-$C_4$ hydroxyalkyl group.

R is an alkyl chain containing 10 to 20, preferably 10 to 18 carbon atoms and can possess one or more double bonds and can be optionally branched. Preferred examples of such alkyl groups are the decyl, lauryl, myristyl, cetyl, palmoleyl, 2-hexyldecyl, stearyl, isostearyl, oleyl, elaidyl, petroselinyl, arachyl, 2-octyldodecyl and gadoleyl groups, as well as their mixtures, as would result from the raw material used or production method. Alkyl groups based on cocoalkyl or tallow fat alkyl groups are preferred for R.

R1 and R2 are independently a $C_1$-$C_4$ alkyl group or a $C_2$-$C_4$ hydroxyalkyl group In this regard, suitable and preferred $C_1$-$C_4$ alkyl groups are the methyl, ethyl, propyl, isopropyl, butyl, 1-methylpropyl, 2-methylpropyl and 1,1-dimethylethyl groups. In this regard, suitable and preferred $C_2$-$C_4$ alkyl groups are the 2-hydroxyethyl, 3-hydroxypropyl and 2-hydroxypropyl groups. Particularly preferably, R1 and R2 are each a methyl group.

In one embodiment of the first subject matter of the invention, the agent has at least one compound of Formula (I) as the zwitterionic surfactant wherein R1 and R2 are each a methyl group and R is a cocoalkyl group.

Such particularly suitable zwitterionic surfactants have the INCI name Coco Betaine and are sold, for example, under the trade name Genagen® KB as an aqueous solution containing 30 wt % active substance.

In order to generate stable foam, the ready-for-use agent has to have a sufficient amount of zwitterionic surfactant. Accordingly, in one embodiment of the first subject matter of the invention, the agent has one or more zwitterionic surfactants of Formula (I) in a total weight fraction of at least 2.5 wt %, preferably at least 3 wt % and particularly at least 4 wt %, based on total weight of the ready-for-use agent.

In order to further improve foam formation and foam stability, it can be inventively preferred to add additional, particularly non-ionic, surfactants to the agent.

Accordingly, in another embodiment of the first subject matter of the invention the agent additionally comprises at least one non-ionic surfactant.

Alkyl polyglycosides as well as alkylene oxide addition products to saturated, linear fatty alcohols, fatty acid esters and fatty acids, each with 2 to 80 moles ethylene oxide per mole fatty alcohol or fatty acid, are preferred non-ionic surfactants. Preparations with excellent properties are also obtained when they comprise fatty acid esters of ethoxylated glycerine as the non-ionic surfactants.

According to a preferred embodiment, the agent has at least one alkyl and/or alkenyl polyglucoside as the non-ionic surfactant. Known non-ionic surfactants of Formula (II) represent alk(en)yl polyglucosides—

$$R^1O\text{-}[G]_p \qquad (II)$$

wherein $R^1$ is an alkyl or alkenyl group containing 4 to 22 carbon atoms, G is a sugar group containing 5 or 6 carbon atoms, and p is a number from 1 to 10.

Alkyl and alkenyl polyglucosides can derive from aldoses or ketoses containing 5 or 6 carbon atoms, preferably from glucose. Preferred alkyl and/or alkenyl polyglucosides are therefore alkyl and/or alkenyl polyglucosides. The index value p in the general Formula (II) represents the degree of polymerization (DP) (i.e., the distribution of mono and polyglucosides), and is a number from 1 to 10. Whereas in a given compound p is a whole number and here above all can assume the values p=1 to 6, the value p for a specific alkyl oligoglucoside is an analytically determined calculated quantity that mostly represents a fractional number. Preferably, alkyl and/or alkenyl polyglucosides are employed with an average degree of oligomerization p of 1.1 to 3.0. From an industrial point of view, such alkyl and/or alkenyl polyglucosides are preferred with degrees of polymerization of 1.7 or less, and particularly from 1.2 to 1.4.

The alkyl or alkenyl group $R^1$ may be derived from primary alcohols containing 4 to 11 and preferably 8 to 10 carbon atoms. Typical examples are butanols, caproyl alcohol, caprylic alcohol, capric alcohol and undecyl alcohol as well as their industrial mixtures, such as those obtained by hydrogenation of industrial fatty acid methyl esters or in the course of the hydrogenation of aldehydes from the Roelen Oxosynthesis. Alkyl polyglucosides with chain lengths $C_8$-$C_{10}$ (DP=1 to 3) are preferred, which result as the low boiling fraction in the separative distillation of industrial $C_8$-$C_{18}$ coco fatty alcohol and which can be contaminated with a fraction of less than 6 wt % of $C_{1-2}$ alcohol, as well as alkyl polyglucosides based on industrial $C_{9/11}$ oxo alcohols (DP=1 to 3). The alkyl or alkenyl group $R^1$ can moreover be derived from primary alcohols containing 12 to 22, preferably 12 to 14 carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol as well as their industrial mixtures that can be obtained as described above. Alkyl polyglucosides based on hydrogenated $C_{12/14}$ coco alcohol with a DP of 1 to 3 are preferred.

Inventively suitable alkyl and/or alkenyl polyglucosides are commercialized under the INCI name Coco-Glucoside and the trade name Plantacare 818 UP or under the INCI name Lauryl-Glucoside and the trade name Plantacare 1200 UP.

The alkyl or alkenyl polyglucosides are preferably present in agents according to the invention in amounts of 0.1 to 20 wt %, based on the ready-for-use agent. Quantities of 1 to 15 wt % are particularly preferred. Quantities of 3 to 8 wt % are quite particularly preferred.

Furthermore, it has proven advantageous if agents according to the invention have at least one additional surfactant different from the alk(en)yl polyglucoside(s). Here, ethoxylated, non-ionic surfactants are preferably added. In this regard, it is particularly advantageous if the additional non-ionic surfactant has an HLB value above 10, preferably above 14. In addition, the non-ionic surfactant has to have a sufficiently high degree of ethoxylation.

Accordingly, in another embodiment of the first subject matter of the invention the agent additionally has at least one ethoxylated surfactant containing at least 30 ethylene oxide units as the non-ionic surfactant.

Besides the appropriately ethoxylated fatty alcohols, the addition products of 30 to 60 mol ethylene oxide on castor oil and hydrogenated castor oil are especially inventively particularly suitable. These specific non-ionic surfactants afford an additional improvement in the foam consistency, particularly with regard to a higher strength, an enhanced fine cell structure and a higher suppleness.

Examples of such suitable surfactants bear the INCI names Steareth-30, Ceteareth30, Oleth-30, Ceteareth-50 or PEG-40 Hydrogenated Castor Oil and PEG-60 Hydrogenated Castor Oil. PEG-60 Hydrogenated Castor Oil is commercialized, for example, under the trade name Cremophor CO 60.

Ethoxylated, non-ionic surfactants are present in agents according to the invention in amounts of 0.1 to 10 wt %, preferably from 0.5 to 8 wt % and particularly preferably from 1.0 to 5.0 wt %, based on total weight of the ready-for-use agent.

Furthermore, in order to achieve the desired foam properties, it is inventively significant for the ready-for-use agent to have a total surfactant content of at least 10 wt %. Agents having at least 11 wt %, preferably at least 12 wt % total surfactant content, based on total weight of the ready-for-use agent, are particularly preferred.

Moreover, it has proven to be advantageous if the ready-for-use preparation is free of cationic surfactants.

Furthermore, it has been found that it is advantageous if the agents contain at least one anionic surfactant in addition to the above cited surfactants. Inventively particularly preferred anionic surfactants are—
- linear and branched fatty acids with 8 to 30 carbon atoms (soaps),
- ether carboxylic acids of the formula R—O—($CH_2$—$CH_2O$)$_x$—$CH_2$—COOH, in which R is a linear alkyl group with 10 to 22 carbon atoms and x=0 or 1 to 16, and
- alkyl sulfates and alkyl polyglycol ether sulfates of the Formula R—(O—$CH_2$—$CH_2$)X—$OSO_3$H, in which R is preferably a linear alkyl group with 8 to 30 carbon atoms and x=0 or 1 to 12.

In a quite particularly preferred embodiment of the present invention, the agents comprise an anionic surfactant in addition to the surfactants that are essential for the invention. Particularly for two-part agents, wherein dye-containing components and oxidizing agents are packaged separately, it has proven advantageous if the anionic surfactant is present in the oxidizing agent preparation and the other surfactants are present in the dye-containing component.

It was surprisingly found that the presence of small amounts of a polymeric thickener had a positive influence on foam stability. Accordingly, in an embodiment of the present invention, the agents comprise at least one polymeric thickener.

Exemplary inventively preferred polymeric thickeners are: Acrylates Copolymer, Acrylamides Copolymer, Acrylamide/Sodium Acrylate Copolymer, Acrylamide/Sodium Acryloyldimethyltaurate Copolymer, Acrylates/Acetoacetoxyethyl Methacrylate Copolymer, Acrylates/Beheneth-25 Methacrylate Copolymer, Acrylates/C10-30 Alkyl Acrylate Crosspolymer, Acrylates/Ceteth-20 Itaconate Copolymer, Acrylates/Ceteth-20 Methacrylate Copolymer, Acrylates/Laureth-25 Methacrylate Copolymer, Acrylates/Palmeth-25 Acrylate Copolymer, Acrylates/Palmeth-25 Itaconate Copolymer, Acrylates/Steareth-50 Acrylate Copolymer, Acrylates/Steareth-20 Itaconate Copolymer, Acrylates/Steareth-20 Methacrylate Copolymer, Acrylates/Stearyl Methacrylate Copolymer, AcrylatesNinyl Isodecanoate Crosspolymer, Acrylic Acid/Acrylonitrogens Copolymer, Agar, Agarose, Alcaligenes Polysaccharides, Algin, Alginic Acid, Ammonium Acrylates/Acrylonitrogens Copolymer, Ammonium Acrylates Copolymer, Ammonium AcryloyldimethyltaurateNinyl Formamide Copolymer, Ammonium AcryloyldimethyltaurateNP Copolymer, Ammonium Alginate, Ammonium Polyacryloyldimethyl Taurate, Amylopectin, Ascorbyl Methylsilanol Pectinate, Astragalus Gummifer Gum, Attapulgite, Avena Sativa (Oat) Kernel Flour, Bentonite, Butoxy Chitosan, Caesalpinia Spinosa Gum, Calcium Alginate, Calcium Carboxymethyl Cellulose, Calcium Carrageenan, Calcium Potassium Carbomer, Calcium Starch Octenylsuccinate, C20-40 Alkyl Stearate, Carbomer, Carboxybutyl Chitosan, Carboxymethyl Chitin, Carboxymethyl Chitosan, Carboxymethyl Dextran, Carboxymethyl Hydroxyethylcellulose, Carboxymethyl Hydroxypropyl Guar, Cellulose Acetate Propionate Carboxylate, Cellulose Gum, Ceratonia Siliqua Gum, Cetyl Hydroxyethylcellulose, Cholesterol/HDI/Pullulan Copolymer, Cholesteryl Hexyl Dicarbamate Pullulan, Cyamopsis Tetragonoloba (Guar) Gum, Diglycol/CHDM/Isophthalates/SIP Copolymer, Dihydrogenated Tallow Benzylmonium Hectorite, Dimethicone Crosspolymer-2, Dimethicone Propyl PG-Betaine, DMAPA Acrylates/Acrylic Acid/Acrylonitrogens Copolymer, Ethylene/Sodium Acrylate Copolymer, Gelatin, Gellan Gum, Glyceryl Alginate, Glycine Soja (Soybean) Flour, Guar Hydroxypropyltri-monium Chloride, Hectorite, Hydrated Silica, Hydrogenated Potato Starch, Hydroxybutyl Methylcellulose, Hydroxyethyl Acrylate/Sodium Acryloyldimethyl Taurate Copolymer, Hydroxyethylcellulose, Hydroxyethyl Chitosan, Hydroxyethyl Ethylcellulose, Hydroxypropylcellulose, Hydroxypropyl Chitosan, Hydroxypropyl Ethylenediamine Carbomer, Hydroxypropyl Guar, Hydroxypropyl Methylcellulose, Hydroxypropyl Methylcellulose Stearoxy Ether, Hydroxypropyl Starch, Hydroxypropyl Starch Phosphate, Hydroxypropyl Xanthan Gum, Hydroxystearamide MEA, Isobutylene/Sodium Maleate Copolymer, Lithium Magnesium Silicate, Lithium Magnesium Sodium Silicate, Macrocystis Pyrifera (Kelp), Magnesium Alginate, Magnesium Aluminum Silicate, Magnesium Silicate, Magnesium Trisilicate, Methoxy PEG-22/Dodecyl Glycol Copolymer, Methylcellulose, Methyl Ethylcellulose, Methyl Hydroxyethylcellulose, Microcrystalline Cellulose, Montmorillonite, Moroccan Lava Clay, Natto Gum, Nonoxynyl Hydroxyethylcellulose, Octadecene/MA Copolymer, Pectin, PEG-800, PEG-Crosspolymer, PEG-150/Decyl Alcohol/SMDI Copolymer, PEG-175 Diisostearate, PEG-190 Distearate, PEG-15 Glyceryl Tristearate, PEG-140 Glyceryl Tristearate, PEG-240/HDI Copolymer Bis-Decyltetradeceth-20 Ether, PEG-100/I PDI Copolymer, PEG-180/Laureth50/TMMG Copolymer, PEG-10/Lauryl Dimethicone Crosspolymer, PEG-15/Lauryl Dimethicone Crosspolymer, PEG-2M, PEG-5M, PEG-7M, PEG-9M, PEG-14M, PEG-20M, PEG-23M, PEG-25M, PEG-45M, PEG-65M, PEG-90M, PEG-1 15M, PEG-160M, PEG-120 Methyl Glucose Trioleate, PEG-180/Octoxyno1-40/TMMG Copolymer, PEG-150 Pentaerythrityl Tetrastearate, PEG-4 Rapeseedamide, PEG-150/Stearyl Alcohol/SMDI Copolymer, Polyacrylate-3, Polyacrylic Acid, Polycyclopentadiene, Polyether-1, Polyethylene/Isopropyl Maleate/MA Copolyol, Polymethacrylic Acid, Polyquaternium-52, Polyvinyl Alcohol, Potassium Alginate, Potassium Aluminum Polyacrylate, Potassium Carbomer, Potassium Carrageenan, Potassium Polyacrylate, Potato Starch Modified, PPG-14 Laureth-60 Hexyl Dicarbamate, PPG-14 Laureth-60 Isophoryl Dicarbamate, PPG-14 Palmeth-60 Hexyl Dicarbamate, Propylene Glycol Alginate, PVP/Decene Copolymer, PVP Montmorillonite, Rhizobian Gum, Ricinoleic Acid/Adipic Acid/AEEA Copolymer, Sclerotium Gum, Sodium Acrylate/Acryloyldimethyl Taurate Copolymer, Sodium Acrylates/Acrolein Copolymer, Sodium Acrylates/Acrylonitrogens Copolymer, Sodium Acrylates Copolymer, Sodium Acrylates/Vinyl Isodecanoate Crosspolymer, Sodium AcrylateNinyl Alcohol Copolymer, Sodium Carbomer, Sodium Carboxymethyl Chitin, Sodium Carboxymethyl Dextran, Sodium Carboxymethyl BetaGlucan, Sodium Carboxymethyl Starch, Sodium Carrageenan, Sodium Cellulose Sulfate, Sodium Cyclodextrin Sulfate, Sodium Hydroxypropyl Starch Phosphate, Sodium Isooctylene/MA Copolymer, Sodium Magnesium Fluorosilicate, Sodium Polyacrylate, Sodium Polyacrylate Starch, Sodium Polyacryloyldimethyl Taurate, Sodium Polymethacrylate, Sodium Polystyrene Sulfonate, Sodium Silicoaluminate, Sodium Starch Octenylsuccinate, Sodium Stearoxy PG-Hydroxyethylcellulose Sulfonate, Sodium Styrene/Acrylates Copolymer, Sodium Tauride Acrylates/Acrylic Acid/Acrylonitrogens Copolymer, Solanum Tuberosum (Potato) Starch, Starch/Acrylates/Acrylamide Copolymer, Starch Hydroxypropyltrimonium Chloride, Steareth-60 Cetyl Ether, Steareth-100/PEG-136/HDI Copolymer, Sterculia Urens Gum, Synthetic Fluorphlogopite, Tamarindus Indica Seed Gum, Tapioca Starch, TEA-Alginate, TEA-Carbomer, Triticum Vulgare (Wheat) Starch, Tromethamine Acrylates/Acrylonitrogens Copolymer, Tromethamine Magnesium Aluminum Silicate, Welan Gum, Xanthan Gum, Yeast Beta-Glucan, Yeast Polysaccharides, *Zea Mays* (Corn) Starch.

From this extensive group, thickeners having at least one monomer of the acrylic acid or methacrylic acid type as well as their derivatives, are particularly advantageous. An inventively quite particularly preferred polymer is the copolymer known under the INCI name Acrylates Copolymer of two or more monomers, chosen from acrylic acid, methacrylic acid and their esters with $C_1$-$C_4$ alkyl groups.

As already discussed, it is particularly advantageous if the polymeric thickener is present in small amounts, preferably in amounts of 0.05 to 2 wt %, particularly 0.1 to 1 wt %, based on total weight of the ready-for-use mixture.

A further improvement in the care properties of the products was achieved by incorporating an extract obtained from and/or with the aid of algae and/or plankton. In particular, the moisture balance of the fibers as well as their gloss could be considerably increased by these extracts. According to the invention, "extracts that are obtained from and/or with the aid of algae and/or plankton" refers to mixtures of active substances obtained either by extraction of algae and/or plankton themselves or by extraction of the aqueous phase surrounding the algae and/or the plankton. Inventively preferred algae and/or plankton types are chosen from the genera Haptophyta, Schlundgeissler (Cryptista), Euglenozoa, Dinozoa, Chlorarachniophyta, Gold algae (Chrysophyta), Silica algae (Bacillariophyta, also known as Diatomae), Brown algae (Phaeophyta), Dinogellatae, Red algae (Rhodophyta), Green algae (Chlorophyta), Picobiliphyta as well as Blue algae (for example Oscillatoria and Spirulina). In the context of the present invention, extracts from Blue algae occurring principally in fresh water are particularly preferred.

Regarding the ways and means of obtaining the inventive extracts from the algae and/or plankton ingredients, there are in principle no limitations. The extraction composition used to prepare the cited algae extracts can be water, alcohols as well as their mixtures. Exemplary preferred alcohols are lower alcohols such as ethanol and isopropanol, particularly polyhydric alcohols such as ethylene glycol, propylene glycol and butylene glycol, both as the sole extraction agent as well as in aqueous mixtures. Blue algae extracts that have been obtained by a water/propylene glycol mixture have proven to be particularly suitable. In this regard, it is particularly suitable if these extraction agents are used in a ratio of 1:10 to 10:1.

Furthermore, it can be inventively preferred to incorporate extracts that have been at least partially decolorized prior to use. This can be carried out, for example, with active carbon. It is likewise possible to incorporate the aqueous breeding solution or culture solution of algae or plankton as the algae or plankton extract into the inventive agents. For this the algae or the plankton are firstly separated from the culture solution by a physical separation method, such as filtration or centrifugation.

In a particularly preferred embodiment, the agent comprises an extract of a Blue alga, preferably a fresh water Blue alga, particularly preferably a Blue alga of the genus *Spirulina*.

Agents according to the invention preferably comprise algae extracts and/or plankton extracts in an amount of 0.001 to 5 wt %, more preferably 0.01 to 2 wt %, relative to the ready-for-use agent.

In addition, it can be inventively preferred if the agents additionally have at least one amino acid and/or at least one protein. Inventively preferred amino acids are arginine, serine, lysine, glycine, tyrosine, proline, glutamine, cysteine and histidine. A surprisingly strong structuring of the hair is enabled by the amino acids and/or the proteins.

It has also been determined that formulating the agents without silicone oils has an advantageous effect on the consistency of the foam.

Compositions according to the invention can have as an additional ingredient at least one ammonium compound from the group ammonium chloride, ammonium carbonate, ammonium bicarbonate, ammonium sulfate and/or ammonium carbamate in an amount of 0.5 to 10, preferably 1 to 5 wt %, based on total composition of the agent.

Furthermore, agents according to the invention can comprise additional active substances, auxiliaries and additives, such as non-ionic polymers (e.g., vinyl pyrrolidinone/vinyl acrylate copolymers, polyvinyl pyrrolidinone, vinyl pyrrolidinone/vinyl acetate copolymers, polyethylene glycols and polysiloxanes); additional silicones such as volatile, non-volatile, linear, branched or cyclic, crosslinked or uncrosslinked polyalkylsiloxanes (e.g., dimethicone or cyclomethicone), polyarylsiloxanes and/or polyalkylarylsiloxanes, particularly polysiloxanes with organofunctional groups, such as substituted or unsubstituted amines (amodimethicone), carboxyl, alkoxy and/or hydroxyl groups (Dimethicone copolyols), linear polysiloxane(A)-polyoxyalkylene(B)-block copolymers, grafted silicone polymers; cationic polymers such as quaternized cellulose ethers, polysiloxanes with quaternary groups, dimethyldiallylammonium chloride polymers, acrylamide-dimethyldiallylammonium chloride copolymers, dimethylaminoethyl methacrylate-vinyl pyrrolidinone copolymers quaternized with diethyl sulfate, vinyl pyrrolidinone-imidazolinium methochloride copolymers and quaternized polyvinyl alcohol; zwitterionic and amphoteric polymers; structurants such as glucose, maleic acid and lactic acid, hair conditioning compounds such as phospholipids (e.g., lecithin and cephalin); perfume oils, dimethyl isosorbide and cyclodextrins; fiber structure improvers, particularly mono-, di- and oligosaccharides such as glucose, galactose, fructose, fruit sugar and lactose; colorants for coloring the agent; anti-dandruff actives such as Piroctone Olamine, Zinc Omadine and Climbazol; amino acids and oligopeptides, particularly arginine and/or serine; animal and/or vegetal based protein hydrolysates such as protein hydrolysates of elastin, collagen, keratin, silk and milk albumin, or protein hydrolysates of almonds, rice, peas, potatoes and wheat, as well as in the form of their fatty acid condensation products or optionally anionically or cationically modified derivatives; vegetal oils such as macadamia nut oil, candle nut oil, palm oil, amaranth seed oil, peach stone oil, avocado oil, olive oil, cocoa oil, rape seed oil, sesame oil, jojoba oil, soja oil, peanut oil, evening primrose oil and tea tree oil; light protective agents such as derivatized benzophenones, cinnamic acid derivatives and triazine; active substances such as pantolactone, allantoin, pyrrolidinone carboxylic acids and their salts as well as bisabolol; polyphenols, in particular hydroxycinnamic acids, 6,7-dihydroxycoumarine, hydroxybenzoic acids, catechol, tannins, leucoanthocyanidine, anthocyanidine, flavanones, flavones and flavonols; ceramides or pseudoceramides; vitamins, provitamins and vitamin precursors, particularly from the groups A, $B_3$, $B_5$, $B_6$, C, E, F and H; plant extracts such as the extracts of aloe vera, angelica, aniseed, apricot, benzoin, bergamot, birch, stinging nettle, calmus, cassis, costic, marshmallow, oak bark, elemi, estragon, spruce needles, galbanum, geranium, ginseng, grapefruit, guaiacum wood oil, green tea, hamamelis, rest harrow, hops, coltsfoot, ginger root, iris, jasmin, camomile, cardamum, clover, burdock root, Scotch fir, kiwi, coconut, coriander, caraway, larch, lavender, lemon grass, lily, lime, linden blossom, litchi, mace, malva, almond, mango, rest harrow, melon, meristem, myrrh, neroli, olibanum, opoponax, orange, patchouli, petitgrain, pine, quendel, rooibos, rose, rosemary, horse chestnut, sandal wood, sage, field horsetail, common yarrow, celery, fir, thyme, juniper, vine leaves, hawthorn, wheat, lady's smock, ylang-ylang, cedar and lemon; fats and waxes such as fatty alcohols, beeswax, Montan wax and paraffins; swelling and penetration substances such as glycerin, propylene glycol monoethyl ether, carbonates, hydrogen carbonates, guanidines, ureas as well as primary, secondary and tertiary phosphates; opacifiers such as latex, styrene/pvp and styrene/acrylamide copolymers; pearlescents such as ethylene glycol mono- and distearate as well as PEG-3 distearate; pigments as well as propellants such as propane-butane mixtures, $N_2O$, dimethyl ether, $CO_2$ and air.

One skilled in the art selects these additional materials as a function of the desired properties of the agent. With regard to further optional ingredients and their amounts used, reference is expressly made to the relevant handbooks known to one skilled in the art, for example, the monograph by K. Schrader, Grundlagen and Rezepturen der Kosmetika, 2nd edition, Huthig Buch Verlag, Heidelberg, 1989. Additional active substances and auxiliaries are preferably incorporated into agents according to the invention in amounts of 0.0001 to 10 wt %, particularly 0.0005 to 5 wt %, based on total weight of the application agent.

In principle, an oxidative coloration of the fibers can take place with atmospheric oxygen in the presence of oxidation dye precursors. However, it is preferred to use a chemical oxidizing agent, particularly when a lightening effect on human hair is desired in addition to the dyeing. This lightening effect may be desired independently of the dyeing method. The presence of oxidation dye precursors is accordingly not a necessary prerequisite for a use of oxidizing agents in the agents according to the invention. Oxidizing agents that come under consideration are persulfates, chlorites and in particular hydrogen peroxide or its addition products onto urea, melamine as well as sodium borate.

According to the invention, the oxidation dyeing agent can also be applied to the hair together with a catalyst that activates the oxidation of the dye precursors (e.g., by atmospheric oxygen). Such catalysts are metal ions, iodides, quinones or certain enzymes.

When using oxidizing agents, the actual dyeing agent is expediently prepared directly prior to use by mixing the preparation of the oxidizing agent with the preparation that comprises at least one oxidation dye precursor. The resulting ready-for-use hair coloration preparation should preferably have a pH in the range 6 to 12. The hair dye is particularly preferably applied in a weakly alkaline milieu. In the context of the present invention, the pH values refer to those measured at a temperature of 22° C.

The addition of complexants is also inventively preferred. Complexants are substances that can complex metal ions. Preferred complexants are chelating agents (i.e., substances that form cyclic compounds with metal ions, wherein a single ligand occupies more than one coordination site on a central atom). Thus in this case, compounds that are normally linear are ring-closed by complex formation with an ion. The number of the bonded ligands depends on the coordination number of the central ion. Suitable and—in the context of the invention—preferred chelating agents include polyoxycarboxylic acids, polyamines, ethylenediaminetetraacetic acid (EDTA) and nitrilotriacetic acid (NTA) and hydroxyethane diphosphonic acids and their alkali metal salts. Inventively preferred complexants are phosphonates, preferably hydroxyalkane or aminoalkane phosphonates and especially 1,1-hydroxyethane-1,1-diphosphonate (HEDP) or its di- or tetrasodium salt and/or ethylenediaminetetramethylene phosphonate (EDTMP) or its hexasodium salt and/or diethylenetriaminepentamethylene phosphonate (DTPMP) or its hepta or octasodium salt. Dipicolinic acid is also inventively preferably used as a complexant. Agents having a combination of an EDTA salt and HEDP and dipicolinic acid are inventively particularly preferred.

The pH is usually adjusted with pH adjustors. The person skilled in cosmetics commonly uses established acidifiers and alkalizers to adjust the pH. The alkalizers that can be used for adjusting the pH are typically chosen from inorganic salts, especially from alkali metals and alkaline earth metals, organic alkalizers, especially amines, basic amino acids and alkanolamines, and ammonia. Inventively preferred acidifiers are food acids such as citric acid, acetic acid, malic acid or tartaric acid, as well as diluted mineral acids.

In addition to the already described and imperatively comprised alkanolamines, the agent can comprise further alkalizers. Inorganic alkalizers according to the invention are preferably chosen from sodium hydroxide, potassium hydroxide, calcium hydroxide, barium hydroxide, sodium phosphate, potassium phosphate, sodium silicate, potassium silicate, sodium carbonate and potassium carbonate. In the context of the invention, the basic amino acids that can be used as an inventive alkalizer are preferably chosen from L-arginine, D-arginine, D,L-arginine, L-lysine, D-lysine, D,L-lysine, particularly preferably L-arginine, D-arginine, D,L-arginine. Finally, ammonia is another preferred alkalizer. The additional alkalizers are preferably present in amounts of 0.05 to 10 wt %, particularly 0.5 to 5 wt %, based on total weight of the ready-for-use agent.

In a particularly preferred embodiment, agents according to the invention are formulated free of ammonia as the alkalizer. In this regard, "free of ammonia" according to the invention means that the ammonia content of the inventive agent is 1 wt % or less, preferably 0.5 wt % or less, and particularly 0.1 wt % or less, based on ready-for-use agent.

In addition, it has proved particularly preferable if the resulting application liquid is formulated to be of low viscosity. Application liquids which, after mixing with the oxidizing agent preparation, exhibit a viscosity of 0 to 2000 mPas (measured at 22° C. in the Brookfield Viscosimeter type RV-T with spindel LV-1 or RV-1 and a speed of 30 rpm) are particularly preferred. According to the invention, a viscosity of 0 to 1000 mPas, measured under the cited conditions, is particularly preferred. According to the invention, a viscosity of 5 to 500 mPas, particularly 10 to 50 mPas (measured under the cited conditions) is quite particularly preferred. It is inventively preferred if the described hair dye preparation is taken up in a suitable dispenser and dispensed for each use. In this regard, the hair dye preparation is dispensed principally in foam form. The foam consistency of the preparation is to be very broadly understood in this context and includes any mixture of a flowable preparation and a gaseous component. In this respect, both flowable as well as essentially solid, stable foam consistencies are included in the subject matter of the invention.

Basically a dispenser according to the invention includes at least one reservoir to receive at least one component of the hair dye preparation and an application device to dispense the hair dye preparation in the form of foam. Here the reservoir is especially designed as a tube-shaped or bottle-shaped container, whereas the application device closes this container that is open on one side. The actual dispensing of the preparation is preferably effected by a suitable pressure source that is integrated into the dispenser, particularly in the reservoir, or by a manual pressure build up initiated by the actual user of the hair dye preparation.

As an example of dispensers with an integrated pressure source according to the invention, one may mention pressure vessels that usually have either a suitable pressure accumulator inside the container (e.g., mechanical) or comprise a propellant, and in this way place the inside of the container under pressure. These types of pressure vessels are usually equipped with suitable valve devices for dispensing the preparation located inside the pressure vessel when the corresponding valve is actuated. Such pressure vessels in conjunction with gaseous and/or liquid propellants are mainly known in the form of aerosol dispensers for the most varied cosmetic applications (e.g., hair styling sprays, hair dye preparations, deodorant sprays, shaving foam/gels, etc.).

Alternatively, manually actuated dispensers can also be used according to the invention. They rely solely on the force exerted by the user in order to dispense a foamed preparation. These types have the advantage that an additional pressure source (e.g., propellant) is not required; this is desirable principally on the grounds of cost and sustainability. These foam dispensers actuated by manual force provide not only for the delivery of the hair dye preparation out of the reservoir to the dispensing outlet, but also for an appropriate foaming of the hair dye preparation. During this foaming or foam formation, the hair dye preparation is basically mixed with a gaseous component, especially air. Specifically, a foaming device that does this is provided for this purpose. According to a first variant of a manually actuatable dispenser, it is designed as a shakable dispenser, having at least one reservoir for receiving the hair dye preparation, and an associated dispensing device for dispensing the foamed hair dye preparation. In this regard the dispensing device in particular is detachably connected to the reservoir. The actual foam formation occurs inside the shakable dispenser by shaking the hair dye preparation inside the reservoir. The shakable dispenser in conjunction with the appropriate movement of the dispenser thereby forms the above cited foaming device. Subsequent to this type of foaming, the foamed hair dye preparation can then be dispensed by the dispensing device.

Another reasonable dispenser variant is provided by the development as a squash or squeeze foam dispenser. A squeeze foam dispenser possesses in addition to the at least one reservoir for receiving the hair dye preparation, an appropriate application device inside which the foaming occurs as well as the subsequent delivery of the hair dye preparation. The hair dye preparation is actually delivered from the reservoir by a force exerted onto the flexible wall of the reservoir. Here, the reversible deformation of the reservoir wall creates a pressure increase inside the reservoir, resulting in the hair dye preparation being forced out of the reservoir. For this to happen the reservoir wall has to be designed to be sufficiently flexible or reversibly deformable. This is ensured by a design thickness of the reservoir wall appropriate to the required application, in conjunction with a suitable choice of material for the reservoir wall. The reservoir wall of a suitable squeeze foam dispenser is preferably made of a polyolefin such as polypropylene (PP), high density polyethylene (HDPE), medium density polyethylene (MDPE), low density polyethylene (LDPE), linear low density polyethylene (LLDPE). Among these, polypropylene (PP) is preferred.

The application device of a squeeze foam dispenser also includes a suitable foaming device for foaming the hair dye preparation. The foaming device is capable of blending a quantity of preparation with a quantity of gas in the appropriate blend ratio in order to generate the desired foam consistency of the hair dye preparation. For this, a flow of preparation and a flow of gas are drawn together into a mixing chamber of the foaming device and blended together by fluid dynamic turbulence. Air is preferably used as the gaseous component for the foam formation and is drawn in either directly from the reservoir or from the surroundings.

The basic functionality of this type of squeeze foam dispenser is also described in the documents WO 2007/086730 A2/A3 and EP 1237660 B1. A squeeze foam dispenser according to the invention can also be correspondingly designed from these patent documents. In particular, the inventive squeeze foam dispenser according to the disclosure of EP 1 237 660 B1 can be designed so that it is possible to use the dispenser in the upright position as well as in an overhead position.

Similarly, the dispenser can also be designed as a pump foam dispenser with at least one reservoir for receiving the hair dye preparation as well as an application device, wherein here the application device possesses a pump device for delivering both the hair dye preparation and the gaseous component, preferably air, and moreover includes an appropriate foaming device. Details of the mode of operation and the structural design of this type of pump dispenser are also found inter alia in the patent documents WO 2007/083206 A1 or WO 2007/091882 A1. In particular, the inventive pump foam dispenser can be designed according to the disclosure of these cited documents.

When using the cited dispenser variants in conjunction with multi-component hair dye preparations that comprise mutually incompatible individual components (e.g. multi-component oxidation hair dye preparations), it must be ensured that the individual components are stored separately up to the actual application of the preparation. This is advantageously achieved by using a plurality of reservoirs for receiving the respective individual components of the hair dye preparation, wherein each reservoir is in fluid connection with the associated application device for delivering the hair dye preparation. This results in the individual components of the hair dye preparation being blended together immediately before being dispensed from the inventive dispenser or when the preparation is actually used. For example, an inventive pump foam dispenser can also be equipped with two or more reservoirs for a plurality of components of the preparation. The structural design and the mode of operation of this type of pump foam dispenser having a plurality of reservoirs is also described in detail in inter alia the patent documents WO 03/078075 A1 and WO 2005/102539 A1. An inventive pump foam dispenser can also be designed according to the disclosure of these documents. In particular, it is conceivable to equip the inventive pump foam dispenser with a plurality of reservoirs and correspondingly with a plurality of pump devices, such that a distinct reservoir as well as a distinct pump device are available for each distinct component of the preparation. In such a case, in order to dispense the preparation the individual components are delivered separately by means of the plurality of pumps. The individual components can then be mixed before or during the foaming of the total hair dye preparation. This has the advantage that only one foaming device is required for all the individual components, and the surfactant content that is required for the foamability of the total hair dye preparation needs to be added to only one of the individual components. Alternatively however, it is also conceivable to provide a plurality of foaming devices and to separately foam each supplied individual component of the hair dye preparation in order only then to mix the foamed individual components. Consequently this requires separately foamable individual components, so that the surfactant fraction required for foamability must be present in each of the individual components.

Having said that, a multi-component hair dye preparation can also be inventively used with one of the above described dispenser variants having only one reservoir and one application device. For this, the reservoir is designed so that it can be recloseably opened. Ideally, the reservoir is closed by the application device, wherein the application device is releasably connected to the reservoir, for example, by a screw- or snap-connection. This opens up the possibility of pre-filling the reservoir during manufacture with a component of the hair dye preparation and to only add additional components of the hair dye preparation into the reservoir shortly before actually using the hair dye preparation. In this connection, the additional components of the hair dye preparation are inside suitable separate containers and are added to the total hair dye product in the form of a kit and are mixed in the reservoir by the user immediately prior to using the hair dye preparation.

In all the listed dispenser variants the individual components of the hair dye preparation can be more easily or better mixed inside the respective application device by using suitable additional mixing devices (e.g., a static mixer, as is also described in WO 2005/102539 A1) or a porous insert element. These types of mixing devices can be advantageously located at a suitable position inside a flow channel for the hair dye preparation in the application device.

Moreover in addition, one or more porous insert elements can be incorporated in order to positively influence the attainable foam consistency inside the foaming device. Such porous insert elements are for example spongy or net-like in structure and are positioned inside the foaming device at suitable places in the flow channel for the hair dye preparation, for example directly upstream of the delivery outlet of the dispenser. This allows the hair dye preparation to flow through the porous insert element and as a result of fluid dynamic turbulence affords a finer and more homogenous foam consistency. The foam consistency can therefore be directly influenced depending on the particular design of the porous insert element. When using a net-like insert element, it has proven expedient to preferably design the net-like insert element with openings of 50 to 220 mesh (mesh=number of openings per inch), particularly preferably 90 to 200 mesh, quite particularly preferably 125 to 175 mesh. When using a plurality of net-like insert elements it is also possible to use insert elements having different openings. In this case, the first upstream-positioned net like insert element preferably has openings of 50 to 220 mesh (mesh=number of openings per inch), particularly preferably 90 to 200 mesh, quite particularly preferably 125 to 175 mesh. The second downstream-positioned net preferably has openings of 160 to 280 mesh, particularly 175 to 245 mesh and quite particularly preferably 180 to 220 mesh. Finally, the number of the porous insert elements used as well as their specific openings or their porosity characteristics can be designed accordingly depending on the relevant type of application.

The application temperatures of the resulting foam can range from 15 to 40° C. After a contact time of 5 to 45 minutes, the hair dye is removed from the hair by rinsing.

A second subject matter of the present invention is a method for dyeing keratinic fibers, in which method an agent according to the invention is discharged as a foam out of a dispenser, is dispersed onto the fibers, then remains on the fibers for a period of 1 to 60 minutes, preferably 5 to 40 minutes, and then washed out of the fibers.

In this regard, the discharged foam can be immediately applied onto the hair roots and then dispersed onto the fibers with the hands or with a mechanical auxiliary. However, it is also conceivable to initially deposit the foam onto a mechanical auxiliary such as a comb, and then with its help disperse the foam on the fibers. Independently of how the foam is applied, it can be inventively preferred to subsequently massage the foam into the hair. It is inventively preferred to make up the application preparation as a 2-component system immediately before the application and then produce the preparation by mixing the components as they are applied.

Accordingly, it is preferred if the agent according to the invention comprising at least one oxidation dye precursor, at least one alkanolamine and at least one zwitterionic surfactant of the Formula (I) is obtained immediately prior to the application by mixing a first agent (A), comprising the at least one oxidation dye precursor, and a second agent (B), comprising an oxidizing agent.

With reference to further preferred embodiments of the method according to the invention, the statement made concerning the agents according to the invention applies mutatis mutandis.

Dyeing is particularly preferably supported by physical measures. An inventive method is when the application is supported by the action of heat, IR and/or UV radiation during the contact time. Another subject matter of the present invention is a kit for dyeing keratinic fibers, the kit having two agents packaged separately from one another, wherein the first agent (A) comprises at least one oxidation dye precursor, the second agent (B) comprises at least one oxidizing agent, and the mixture of agents (A) and (B) results in an agent having at least one oxidation dye precursor, at least one alkanolamine as well as at least one zwitterionic surfactant of Formula (I). A kit is particularly preferred that additionally comprises a dispenser suitable for discharging the mixture of the agents (A) and (B) in the form of a foam.

With reference to further preferred embodiments of the kit according to the invention, the statement made concerning the agents according to the invention applies mutatis mutandis.

EXAMPLES

The following formulations were produced. Unless otherwise stated, the quantities are understood to be in weight percent.

1. Dye Solutions

| Raw material | Inventive dye solution F1 | Non-inventive dye solution F2 |
|---|---|---|
| Plantacare ® 818 UP | 25.00 | 20.00 |
| Dehyton ® K | — | 26.00 |
| Genagen ® KB | 30.00 | — |
| Cremophor ® CO 60 | 3.00 | 3.00 |
| Tetrasodium EDTA | 0.20 | 0.20 |
| p-Toluylenediamine sulfate | 2.31 | 2.31 |
| 2-Amino-4-(2-hydroxyethyl)aminoanisole sulfate | 0.03 | 0.03 |
| Resorcinol | 0.89 | 0.89 |
| m-Aminophenol | 0.26 | 0.26 |
| Sodium sulfite | 0.20 | 0.20 |
| Ascorbic acid | 0.05 | 0.05 |
| Monoethanolamine | 10.00 | 10.00 |
| Eau Vitale d'algue bleue ® | 2.0 | 2.0 |
| Perfume | qs | qs |
| Water | ad 100 | ad 100 |

2. Developer Preparations

| Raw material | E1 | E1-DK |
|---|---|---|
| Dipicolinic acid | 0.10 | 0.10 |
| Disodium pyrophosphate | 0.03 | 0.03 |
| Aculyn ® 33A | 2.50 | 2.50 |
| Texapon ® NSO | 2.00 | 2.00 |
| Cremophor ® CO60 | | 2.00 |
| Eumulgin ® L | | 0.40 |
| Sodium hydroxide (aqueous 45% conc.) | 0.73 | |
| Turpinal ® SL | 1.50 | 1.50 |
| Hydrogen peroxide (aqueous, 50% conc.) | 15.20 | 15.20 |
| Water | ad 100 | ad 100 |

3. Index of the Commercial Products

Aculyn® 33A ca. 28% solids in water; INCI name: Acrylates Copolymer

Cremophor® CO60 INCI name: PEG-60 Hydrogenated Castor Oil (BASF)

Dehyton® K ca. 30% active substance; INCI-name: Aqua (Water), Cocamidopropyl Betaine (Cognis)

Eau Vitale d' algue bleue ca. 0.1-0.99 wt % active substance; INCI name: Aqua (Water), Plankton Extract, Penoxyethanol (Soliance)

Eumulgin® L INCI name: PPG-1-PEG-9 Lauryl Glycol Ether (Cognis)

Plantacare® 818UP ca. 51-53% active substance content; INCI name: Coco-Glucoside, Aqua (Water) (Cognis)

Texapon® NSO ca. 27.5% active substance; INCI name: Sodium Laureth Sulfate (Cognis)

Turpinal® SL ca. 58-61% active substance content; INCI-name: Etidronic Acid, Aqua (Water)) (Solutia)

4. Comparative Tests

Both dye solutions F1 and F2 were produced by methods commonly used by persons skilled in the art. After a short time the dye preparation F2 produced an intensive amine-like odor that was described by the vast majority of test persons as decidedly unpleasant. This odor also remained after mixing with one of developer preparations E1 or E1-DK. In contrast, the inventive dye preparation F1 itself or when mixed with the developer preparations did not exhibit any unwanted odor development.

5. Dyeing

5.1 Application with a Squeeze Foam Dispenser

Oxidizing agent preparation E1 (60 ml) was placed in a squeeze foam dispenser. Immediately prior to application the dye solution according to the invention F1 (60 ml) was carefully added such that no foam formation occurred. The squeeze bottle was then carefully turned upside down and back several times, so as to effect a thorough mixing of the components without extensive foaming. The resulting application preparation had a viscosity of 15 mPas (measured at 22° C. in the Brookfield Viscosimeter type RV-T with spindle LV-1 and at a speed of 30 rpm) and a pH of 9.5.

The foam was discharged directly onto the hair line by pressing the squeeze foam dispenser, the hair was then wetted and finally the foam was evenly distributed into the fibers with a comb. After a contact time of 30 minutes at room temperature the hair was thoroughly rinsed with water, shampooed and dried with a hair-dryer.

The hair was dyed to a rich dark brown, showed a perfect color balance from the roots to the tips of the hair and an excellent gloss.

5.2 Application with a Pump Foam Dispenser

Oxidizing agent preparation E1 (60 ml) was placed in a pump foam dispenser. Immediately prior to application, dye preparation F1 (60 ml) was carefully added so that no foam formation occurred. The pump dispenser was then carefully turned upside down and back several times, providing a thorough mixing of the components without extensive foaming. The resulting application preparation had a viscosity of 12 mPas (measured at 22° C. in the Brookfield Viscosimeter type RV-T with spindle LV-1 and at a speed of 30 rpm) and a pH of 9.5.

Using the pump head, the foam was initially discharged into the palm of the hand and then applied to the hair line and the hair; finally the foam was evenly distributed into the fibers with a comb. After a contact time of 30 minutes at room temperature the hair was thoroughly rinsed with water, shampooed and dried with a hair-dryer.

The hair was dyed to a rich dark brown, showed a perfect color balance from the roots to the tips of the hair and an excellent gloss.

5.3 Application with a Pump Foam Dispenser Having a Plurality of Reservoirs Oxidizing agent preparation E1-DK (60 ml) and the dye preparation F1 (60 ml) were placed in both of the storage chambers of a pump foam dispenser having two reservoirs. The application preparation obtained by pumping had a pH of 9.5.

Using the linked pump heads, the foam was initially discharged out of the pump foam dispenser into the palm of the hand and then applied to the hair line and the hair; finally the foam was evenly distributed into the fibers with a comb. After a contact time of 30 minutes at room temperature the hair was thoroughly rinsed with water, shampooed and dried with a hair-dryer.

The hair was dyed to a rich dark brown, showed a perfect color balance from the roots to the tips of the hair and an excellent gloss.

We claim:

1. An agent for dyeing keratinic fibers comprising in a cosmetically acceptable carrier:
   at least one oxidation dye precursor,
   at least one alkanolamine, and
   at least one zwitterionic surfactant according to Formula (I),

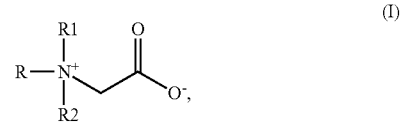

wherein
R is a saturated or unsaturated $C_{10}$-$C_{20}$ alkyl chain, and
R1 and R2 are each independently a $C_1$-$C_4$ alkyl group or a $C_2$-$C_4$ hydroxyalkyl group.

2. The agent according to claim 1, wherein the alkanolamine is monoethanolamine.

3. The agent according to claim 1, wherein R1 and R2 are each a methyl group and R is a cocoalkyl group.

4. The agent according to claim 1, comprising one or more zwitterionic surfactants of the Formula (I) in a total weight fraction of at least 2.5 wt %, based on total weight of the ready-for-use agent.

5. The agent according to claim 1 further comprising at least one non-ionic surfactant.

6. The agent according to claim 5, wherein the non-ionic surfactant is at least one alkyl polyglucoside and/or alkenyl polyglucoside.

7. The agent according to claim 5, wherein the non-ionic surfactant is at least one ethoxylated surfactant containing at least 30 ethylene oxide units.

8. The agent according to claim 5, wherein the non-ionic surfactant is a combination of at least one alkyl polyglucoside and at least one ethoxylated surfactant containing at least 30 ethylene oxide units.

9. The agent according to claim 1, wherein the agent comprises a total surfactant content of at least 10 wt %, based on total weight of the ready-for-use agent.

10. The agent according to claim 1, wherein the agent is free of ammonia.

11. A method for dyeing keratinic fibers comprising:
discharging an agent according to claim 1 as a foam out of a dispenser,
dispersing the foamed agent onto the fibers,
leaving the dispersed agent on the fibers for a period of 1 to 60 minutes, and
washing the agent out of the fibers.

12. The method according to claim 11, wherein the agent is obtained immediately prior to the application by mixing a first agent (A), comprising at least one oxidation dye precursor, and a second agent (B), comprising at least one oxidizing agent.

13. A kit for dyeing keratinic fibers comprising:
at least two separately packaged agents,
wherein a first agent (A) comprises at least one oxidation dye precursor,
a second agent (B) comprises an oxidizing agent, and
the mixture of agents (A) and (B) results in an agent according to claim 1.

14. The kit according to claim 13, further comprising a dispenser suitable for discharging the mixture of the agents (A) and (B) in the form of a foam.

* * * * *